United States Patent
Aki et al.

(10) Patent No.: US 6,630,590 B1
(45) Date of Patent: Oct. 7, 2003

(54) PROCESS FOR PRODUCING CARBOSTYRIL DERIVATIVES

(75) Inventors: Shinji Aki, Tokushima (JP); Muneaki Kurimura, Tokushima (JP); Takao Nishi, Tokushima (JP); Junichi Minamikawa, Naruto (JP); Michiaki Tominaga, Tokushima (JP); Norihiro Fukuyama, Tokushima (JP); Akihiro Yamamoto, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/208,740

(22) Filed: Aug. 1, 2002

Related U.S. Application Data

(63) Continuation-in-part of application No. 09/869,264, filed on Aug. 5, 2002.

(51) Int. Cl.[7] ...................... C07D 215/16; C07D 215/20
(52) U.S. Cl. ........................................ 546/158; 546/157
(58) Field of Search ................................. 546/157, 158

(56) References Cited

U.S. PATENT DOCUMENTS

| 4,277,479 A | 7/1981 | Nishi et al. ................. 424/258 |
| 2002/0099213 A1 | 7/2002 | Mendelovichi et al. ..... 546/158 |

FOREIGN PATENT DOCUMENTS

| ES | 8702401 A | | 3/1987 |
|---|---|---|---|
| JP | 56045414 | * | 4/1981 |
| JP | 56046810 | * | 4/1981 |
| JP | 56-49378 | | 5/1981 |
| JP | 56049378 | | 5/1981 |
| JP | 58059980 | * | 4/1983 |
| JP | 58077880 | * | 5/1983 |
| JP | 1265051 | | 10/1989 |
| JP | 6100487 | | 4/1994 |
| JP | 11152243 | | 6/1999 |
| WO | WO 00/57881 | | 10/2000 |
| WO | WO 2/14283 | | 2/2002 |
| WO | WO 02/14283 | | 2/2002 |

OTHER PUBLICATIONS

H.H. Freedman et al., "An Improved Williamson Ether Synthesis Using Phase Transfer Catalysis," Tetrahedron Letters No. 38, pp. 3251–3254, 1997(**).

T. Nishi et al., "Studies on 2–Oxoquinoline Derivatives as Blood Platelet Aggregation Inhibitors. II. 6–[3(1–Cyclohexyl–5–Tetrazolyl) Propoxy]–1, 2–Dihydro–2–Oxoquinoline and Related Compounds", Chem. Pharm. Bull., vol. 31, No. 4, pp. 1151–1157, (1982)(**).

The Summary of the 29th Symposium on the Chemistry of Natural Products, pp. 41–43 (1994) (English translation of the Certificate and partial English translation are attached thereto.).

Nishi, CA 99:98806, abstract of Chem & pharm bull, 1983, 31(4), 1151–1157.*

Nishi, CA 103:141893, abstract of Chem & Pharm Bull, 1985, 33(3), 1140–1147.*

The Summary of the 29th Symposium on the Chemistry of Natural Products, pp. 41–43 (1994) (full English translation).

(List continued on next page.)

*Primary Examiner*—D. Margaret Seaman
(74) *Attorney, Agent, or Firm*—Finnegan, Henderson, Farabow, Garrett, and Dunner, LLP

(57) ABSTRACT

The present invention provides a process for producing carbostyril derivatives (I) which are known to be useful as medical drug such as antithrombotic agent, cerebral circulation improver, anti-inflammatory agent, antiulcer agent, etc. in a high yield and a high purity. The carbostyril derivatives (I) can be produced by reacting a carbostyril derivative (II) with a tetrazole derivative (III) in the presence of a phase transfer catalyst.

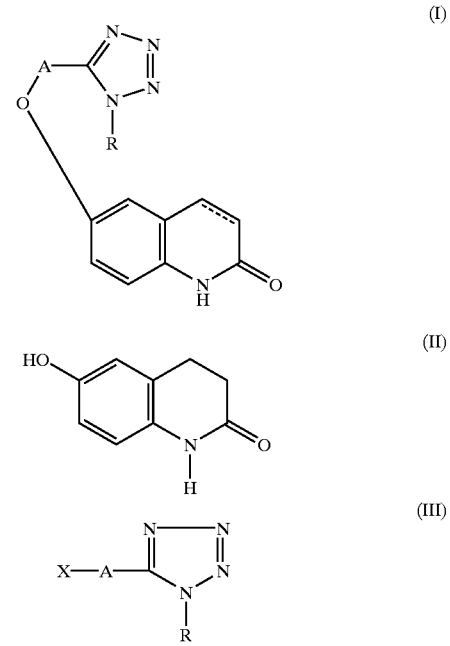

20 Claims, No Drawings

OTHER PUBLICATIONS

Japanese Pharmaceutical Codex, p. 836839 (1997) (full English translation).

Starks; Liotta; *Phase Transfer Catalysis,* Academic Press: NY, 1978, pp. 128–138.

Weber; Gokel; *Phase Transfer Catalysis in Organic Synthesis,* Springer: NY, 1977, pp. 73–84.

A. Mckillop; J.C. Fiaud; R.P. Hug, *Tetrahedron,* vol. 30, p. 1379–1382 (1974).

P.M. Quan; S.R. Kron, *C.A.* vol. 86, 189 480 (1977).

J.D. Reinheimer, J.P. Douglass, H. Leister, M.B. Voelkel, *J. Org. Chem.,* vol. 22, p. 1743–1745 (1957).

B.R. Baker, F.J. McEvoy, *J. Org. Chem.,* vol. 20, p. 136–142 (1955).

A. Cohen, J.W. Haworth, E.H. Hughes, *J. Chem. Soc.,* p. 4374–4383 (1952).

J. Ugelstad, T. Ellingsen, A. Berge, *Acta Chem. Scand.* vol. 20, p. 1593–1598 (1966).

R.L. Merker, M.J. Scott, *J. Org. Chem.* vol. 26, p. 5180–5182 (1961).

J. March, *Advanced Organic Chemistry,* Fourth Edition, John Wiley & Sons: NY, 1992, pp. 362–365, pp. 386–387.

T. Nishi et al., "*Studies on 2–oxoquinoline Derivatives as Blood Platelet Aggregation Inhibitors. I. alkyl 4–(2–Oxo–1, 2,3,4–tetrahydro–6–quinolyloxy) butyrates and related compounds*", Chem. Pharm. Bull., vol. 31, No. 3, pp. 798–810, (1983).

Nishi et al.; "Studies on 2–Oxoquinoline Derivatives as Blood Platelet Aggregation Inhibitors. II. 6–[3–(1–Cyclohexyl–5–Tetrazolyl)Propoxy]–1, 2–Dihydro–2–Oxoquinoline and Related Compounds"; Chem. Pharm. Bull., vol. 31, No. 4, pp. 1151–1157, (1983).

Freedman et al.; "An Improved Williamson Ether Synthesis Using Phase Transfer Catalysis"; Tetrahedron Letters No. 38, pp 3251–3254, 1975.

Chin–Hsien et al., "The Use of Phase–Transfer Catalysis For The Synthesis of Phenyl and 8–Quinolinyl Ethers," Synthesis, pp. 858–861 (1982).

G. Bram et al., "Solid–Liquid Phase Transfer Catalysis Without Solvent: A Mild And Efficient Preparation Of Mono And Di–Ethers Derived From 8–Hydroxyquinoline," Synthetic Communications, 14(9), pp. 889–898 (1984).

Japanese Pharmaceutical Codex, p. 836–839 (1997) (Partial English translation is attached thereto.).

The Merck Index, p. 382 (1996).

A.P. Bashall et al., "A Convenient, High–Yielding Method For The Methylenation of Catechols," Tetrahedron Letters, No. 40, pp. 3489–3490 (1975).

U.S. application No.: 60/225,362, "Novel synthesis for preparing cilostazol", Mendelovichi, M. et al., Aug. 14, 2002.

U.S. application No.: 10/208,738, "Process for producing carbostyril derivatives", Aki, S. et al., Aug. 1, 2002.

* cited by examiner

PROCESS FOR PRODUCING CARBOSTYRIL DERIVATIVES

CROSS-REFERENCE TO RELATED APPLICATION

This application is a continuation-in-part application of U.S. Ser. No. 09/869,264 filed of Aug. 5, 2002 which contents are all incorporated herein by reference.

TECHNICAL FIELD

The present invention relates to a novel process for producing carbostyril derivatives, and more particularly to a novel process for producing carbostyril derivatives represented by the following general formula (I):

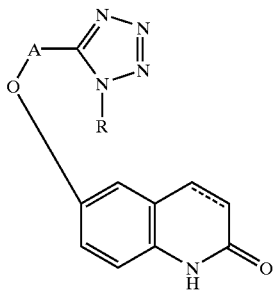

(I)

wherein A represents a lower alkylene group; R represents a cycloalkyl group; and the bond between the 3- and 4-positions of the carbostyril skeleton represents a single bond or a double bond.

BACKGROUND ART

The compound represented by the above-mentioned general formula (I), namely the objective compound of the present invention, is known to be useful as an antithrombotic agent, a cerebral circulation improver, an anti-inflammatory agent, an antiulcer agent, a hypotensive agent, an antiasthmatic agent, and a phosphodiesterase inhibitor, etc. (see: JP-A-56-49378 and U.S. Pat. No. 4,277,479).

The carbostyril derivatives represented by the general formula (I) have so far been produced by reacting a carbostyril derivative represented by the following general formula (II):

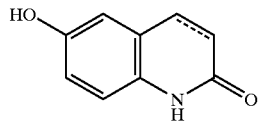

(II)

wherein the bond between the 3- and 4-positions of the carbostyril skeleton is as defined above, with a tetrazole derivative represented by the following general formula (III'):

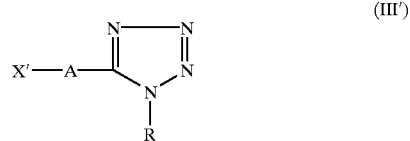

(III')

wherein X' represents a halogen atom, and A and R are as defined above, in the presence of an inorganic base or an organic base (see: JP-A-56-49378; U.S. Pat. No. 4,277,479; and Chem. Pharm. Bull., 31(4), 1151–1157 (1983)).

DISCLOSURE OF THE INVENTION

According to the above-mentioned known process, the yield of the compound of general formula (I) is as low as about 50 to 74%, because there is also formed a compound in which the tetrazole derivative of general formula (III') has reacted not only with the hydroxyl group of the carbostyril derivative of general formula (II) but also with the 1-position of the carbostyril derivative of general formula (I) simultaneously. Since the thus formed contaminative impurity is difficult to remove, production of a compound of general formula (I) having a high purity has required a complicated process of purification.

It is an object of the present invention to provide a process for producing a carbostyril derivative represented by the general formula (I) at a low cost and by a simple procedure. It is another object of the present invention to provide a process for producing a carbostyril derivative represented by the general formula (I) without any complicated process of purification, in a high yield, and in a high purity. It is yet another object of the present invention to provide an industrially advantageous process for producing the carbostyril derivatives represented by the general formula (I).

Further, on the basis of the growing conscious to international environmental conservation in recent years, great demands become arisen in a chemical industry to make every effort decreasing use of the solvents and reagents pointed out the harmfulness, and preventing those materials from discharging into the environment. In order to fulfil those demands, established processes have to be down for a consideration, alternative raw materials, reagents and solvents being less harmful have to be found out, and the processes having higher conversion rate, yield and selectivity have to be developed; so that the environmental load can be diminished. Under the circumstances with these social demands, it is further object of the present invention to provide a process being safe for the environment, for producing a carbostyril derivative represented by the general formula (I) with using phase transfer catalyst in water.

In view of the above-mentioned present situation, the present inventors have conducted various studies with the aim of achieving the above-mentioned objects. As a result, it has been found in the process of the studies surprisingly that, when a phase-transfer catalyst is used as a catalyst, a compound of general formula (I) given by a reaction between the hydroxyl group of the carbostyril derivative of general formula (II) and the tetrazole derivative of general formula (III') is formed, and a compound given by the reaction between the 1-position of the carbostyril derivative of general formula (I) and the tetrazole derivative of general formula (III') is scarcely formed, and the reaction progresses position-specifically, and thereby the objects of the present invention can be achieved. Based on this finding, the present invention has been accomplished.

According to the present invention, the objective carbostyril derivative represented by the general formula (I) can be obtained in a high yield and a high purity by reacting a carbostyril derivative represented by the following general formula (II):

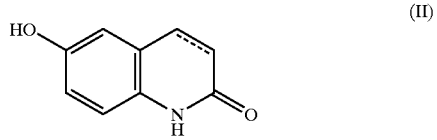
(II)

wherein the bond between the 3- and 4-positions of the carbostyril skeleton represents a single bond or a double bond, with a tetrazole derivative represented by the following general formula (III):

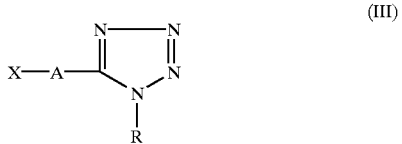
(III)

wherein X represents a halogen atom or a group causing the same substitution reaction as that caused by halogen atom, A represents a lower alkylene group, and R represents a cycloalkyl group, in the presence of a phase-transfer catalyst.

According to the process of the present invention, the hydroxyl group of the carbostyril derivative of general formula (II) and the tetrazole derivative of the general formula (III) can be made to react selectively and thereby the objective carbostyril derivative of general formula (I) can be produced on an industrial scale, at a low cost, by a simple procedure, in a high yield and in a high purity.

BEST MODE FOR CARRYING OUT THE INVENTION

As examples of the lower alkylene group represented by A in the general formulas (I) and (III) of this specification, mention can be made of, straight chain or branched chain alkylene groups having 1–6 carbon atoms such as methylene, ethylene, propylene, tetramethylene, 2-ethylethylene, pentamethylene, hexamethylene, 2-methyltrimethylene, 2,2-dimethyl-trimethylene, 1-methyltrimethylene and the like. Among these lower alkylene groups, particularly preferred is tetramethylene group.

As the cycloalkyl group represented by R in the general formulas (I) and (III), mention can be made of, for example, cycloalkyl groups having 3–8 carbon atoms such as cyclopropyl, cyclobutyl, cyclopentyl, cyclohexyl, cycloheptyl, cyclooctyl and the like. Among these cycloalkyl groups, particularly preferred is cyclohexyl group.

As the halogen atom represented by X in the general formula (III), mention can be made of fluorine atom, chlorine atom, bromine atom and iodine atom, among which particularly preferred is chlorine atom.

As specific examples of the group causing the same substitution reaction as that caused by the halogen atom represented by X in the compound of general formula (III), mention can be made of lower alkanesulfonyloxy group, arylsulfonyloxy group, aralkylsulfonyloxy group and the like. As specific examples of the lower alkanesulfonyloxy group, mention can be made of methanesulfonyloxy, ethanesulfonyloxy, isopropanesulfonyloxy, propanesulfonyloxy, butanesulfonyloxy, tert-butanesulfonyloxy, pentanesulfonyloxy, hexanesulfonyloxy and the like. As specific examples of the arylsulfonyloxy group, mention can be made of substituted or unsubstituted arylsulfonyloxy groups such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, α-naphthylsulfonyloxy and the like. As specific examples of the aralkylsulfonyloxy group, mention can be made of substituted or unsubstituted aralkylsulfonyloxy groups such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulonyloxy, 4-methoxybenzylsulfonyloxy, 3-chlorobenzylsulfonyloxy, α-naphthylmethylsuflonyloxy and the like. Among the groups represented by X, particularly preferred are halogen atoms.

As the bond between the 3- and 4-positions of the carbostyril skeleton in the general formulas (I) and (II), a single bond is particularly preferred.

Next, the process of the present invention will be explained in more detail with reference to reaction schemes.

Reaction Scheme -1

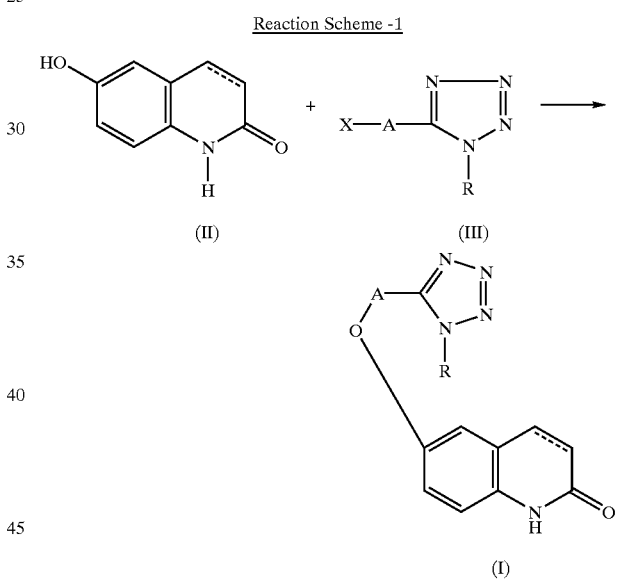

wherein X, A, R and the bond between the 3- and 4-positions of the carbostyril skeleton are as defined above.

In the reaction Scheme-1, the reaction between a compound of general formula (II) and a compound of general formula (III) is carried out in an appropriate solvent in the presence of a phase-transfer catalyst and further a basic compound. As the solvent used herein, all the inert solvents can be used so far as they exercise no adverse influence on the reaction. Examples of the solvent usable include water; alcohols such as methanol, ethanol, propanol, isopropyl alcohol, butanol, ethylene glycol and the like; ethers such as dimethyl ether, diethyl ether, diisopropyl ether, t-butyl methyl ether, tetrahydrofuran, dioxane, monoglyme, diglyme and the like; ketones such as acetone, methyl ethyl ketone, ethyl isobutyl ketone and the like; aromatic hydrocarbons such as benzene, o-dichlorobenzene, chlorobenzene, toluene, xylene and the like; esters such as methyl acetate, ethyl acetate, butyl acetate and the like; aprotic polar solvents such as N,N-dimethylformamide, dimethyl sulfoxide, hexamethylphosphoramide and the like; and mixtures thereof. Among these solvents, particularly preferred are mixtures of water and an aromatic hydrocarbon such as benzene, o-dichlorobenzene, chlorobenzene, toluene, xylene and the like, and water itself alone.

As the basic compound, known ones can be used extensively. Examples thereof include inorganic bases such as sodium hydroxide, potassium hydroxide, cesium hydroxide, lithium hydroxide, sodium carbonate, potassium carbonate, cesium carbonate, lithium carbonate, lithium hydrogen carbonate, sodium hydrogen carbonate, potassium hydrogen carbonate, silver carbonate and the like; alkali metals such as sodium, potassium and the like; alcoholates such as sodium methylate, sodium ethylate and the like; metallic salts of organic acids such as sodium acetate and the like; and organic bases such as triethylamine, diisopropylethylamine, pyridine, N,N-dimethylaniline, N-methylmorpholine, 4-dimethylaminopyridine, 1,5-diazabicyclo-[4.3.0]non-5-ene (DBN), 1,8-diazabicyclo[5.4.0]undec-7-ene (DBU), 1,4-diazabicyclo[2.2.2]octane (DABCO) and the like; and mixtures thereof. Among these bases, inorganic bases such as potassium carbonate, cesium carbonate, lithium carbonate, lithium hydroxide, lithium hydrogen carbonate, sodium hydroxide, potassium hydroxide, potassium hydrogen carbonate, sodium carbonate, sodium hydrogen carbonate, and the like; and mixtures thereof are particularly preferred.

As the phase transfer catalyst, mentioned can be made of, for example, quaternary ammonium salts substituted with a residue selected from the group consisting of straight or branched chain alkyl group having 1–18 carbon atoms, phenyl lower alkyl group including a straight or branched chain alkyl group having 1 to 6 carbon atoms which is substituted by a phenyl group and phenyl group, such as tetrabutylammonium chloride, tetrabutylammonium bromide, tetrabutylammonium fluoride, tetrabutylammonium iodide, tetrabutylammonium hydroxide, tetrabutylammonium hydrogen sulfate, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzylmethyloctadecanylammonium chloride, methyltridecanylammonium chloride, benzyltripropylammonium chloride, benzyltriethylammonium chloride, phenyltriethylammonium chloride, tetraethylammonium chloride, tetramethylammonium chloride and the like; phosphonium salts substituted with a residue selected from the group consisting of straight or branched chain alkyl groups having 1–18 carbon atoms such as tetrabutylphosphonium chloride and the like; and pyridinium salts substituted with a straight or branched chain alkyl group having 1–18 carbon atoms such as 1-dodecanylpyridinium chloride and the like. Among these phase transfer catalysts, quaternary ammonium salts substituted with a straight or branched chain alkyl group having 1–18 carbon atoms such as tetrabutylammonium chloride and the like are particularly preferred. As the salt-forming ions in these salts, hydroxyl ion, hydrogen sulfate ion and halogen ions are preferred, among which chlorine ion is particularly preferred. If desired, sodium sulfite or the like may be added to the reaction system of the above-mentioned reaction for the purpose of preventing the coloration caused by oxidation.

The reaction is carried out usually at a temperature not lower than ambient temperature and not higher than 200° C., and preferably at a temperature of 50–150° C. The reaction time is usually from about one hour to about 10 hours. It is recommended to use the compound (III) usually in an amount of at least 0.5 mol, preferably 0.5–1.5 mol per mol of the compound (II) and more preferably 1.1 to 1.5 mol per mol of the compound (II), to use the basic compound usually in an amount of 1–5 mol per mol of the compound (II), and to use the phase transfer catalyst usually in an amount of 0.1–1 mol and preferably 0.1–0.5 mol per mol of the compound (II).

The reaction may be carried out with circulating the reaction mixture by continuous disperser. The reaction mixture is repeatedly introduced into the continuous disperser and pulverized therein, then returned to the reaction vessel so as to circulate the reaction mixture constantly. The circulation of the reaction mixture can prevent the crystals of the objective product represented by the formula (I) from adhering with each other to make big agglomerates.

The compound of general formula (I) obtained by the above-mentioned reaction can easily be isolated by the conventional separating means. As said separating means, mention can be made of, for example, extraction method using a solvent, dilution method, recrystallization method, column chromatography, preparative thin layer chromatography, etc.

EXAMPLE

Next, the process of the present invention is more concretely explained below with reference to examples. The invention is by no means limited thereby.

Example 1

Into a three-necked flask having a capacity of 300 ml were introduced 10.00 g of 6-hydroxy-3,4-dihydrocarbostyril, 16.36 g of 1-cyclohexyl-5-(4-chlorobutyl)-1,2,3,4-tetrazole, 10.16 g of potassium carbonate, 3.00 g of tetrabutylammonium chloride, 0.05 g of sodium sulfite, 30 ml of toluene and 50 ml of water. The content of the flask was heated under reflux for 8 hours with stirring. After cooling the reaction mixture to ambient temperature, the deposited crystalline product was collected by filtration and washed with 50 ml of water. Then, the crude crystal thus obtained was introduced into 70 ml of 90% methanol cooled to 5° C., and stirred at 5° C. for 10 minutes for the sake of washing. The crystal was collected by filtration and further washed on the suction filter with 20 ml of 90% methanol cooled to 5° C. The crystal was dried to obtain 21.46 g (yield 95%) of 6-[4-(1-cyclohexyl-1,2,3,4-tetrazol-5-yl)butoxy]-3,4-dihydrocarbostyril as a colorless needle-like crystalline product.

Purity: 99.80%; m.p.: 158–159° C.

The purity was measured by high performance liquid chromatography under the following conditions:

Column: YMC Pack SIL A-002 (manufactured by YMC Co.)

Moving phase: dichloromethane/n-hexane/methanol=20/10/1

Detector: UV, 254 nm

Flow rate: 0.90 ml/min.

Retention time: 4.7 min.

Example 2

Into a flask having a capacity of 200 ml were introduced 12.00 g of 6-hydroxy-3,4-dihydrocarbostyril, 19.60 g of 1-cyclohexyl-5-(4-chlorobutyl)-1,2,3,4-tetrazole, 8.20 g of 50% aqueous solution of tetrabutylammonium chloride, 12.20 g of potassium carbonate, 0.60 g of sodium sulfite and 60 ml of water. The content of the flask was heated under reflux for 8 hours with stirring. After the reaction, the reaction mixture was cooled to ambient temperature, and the deposited crude crystal was once collected by filtration. After washing the crystal firstly with 36 ml of methanol and then with 60 ml of water, the crystal was again introduced into a flask having a capacity of 200 ml and heated under reflux together with 84 ml of methanol for 2 hours. The solution thus obtained was cooled to 10° C. The crystal was collected by filtration, washed firstly with 24 ml of methanol and then with 24 ml of water, and dried at 80° C. Thus, 23.84 g (yield 87.7%) of 6-[4-(1-cyclohexyl-1,2,3,4-tetrazol-5-yl)butoxy]-3,4-dihydrocarbostyril was obtained as a colorless needle-like crystalline product.

Purity: 99.89%; m.p.: 158–159° C.

The purity was measured by high performance liquid chromatography (HPLC) under the same conditions as in Example 1.

Example 3

Into a reaction vessel having a capacity of 100 L were introduced 5 kg of 6-hydroxy-3,4-dihydrocarbostyril (30.64 mol), 8.2 kg of 1-cyclohexyl-5-(4-chlorobutyl)-1,2,3,4-tetrazole (33.78 mol), 4.7 kg of potassium carbonate (34.01 mol), 1.0 kg of sodium hydroxide (25 mol), 3.5 kg of 50% aqueous solution of tetrabutylammonium chloride (6.30 mol), 0.25 kg of sodium sulfite (1.98 mol), and 25 L of water. The mixture of the reactants was heated at 85° C. (80~90° C.) for 6 hours with circulating by continuous disperser (pipeline homomixer PL-SL manufactured by TOKUSHUKIKA KOGYO CO. LTD.). After the completion of the reaction, the reaction mixture was cooled to around 50° C. and 15 L of methanol were added thereinto. The reaction mixture with methanol was heated under reflux for 30 minutes. The obtained reaction mixture was cooled to 10 to 20° C. for 30 minutes or more, and the crystals were separated out. The obtained crystals were washed with 25 L of water, 15 L of methanol, and 25 L of water in this order, then dried at 80° C. for about 10 hours. Thus, 10.87 kg (yield: 95.95%) of 6-[4-(1-cyclohexyl-1,2,3,4-tertazol-5-yl)butoxy]-3,4-dihydrocarbostyril was obtained as colorless needle-like crystal.

Purity: 99.71%; m.p.: 158–159° C.

The purity was measured by high performance liquid chromatography (HPLC) under the same conditions as in Example 1.

Example 4

Into a flask having a capacity of 500 ml were introduced 30 g of 6-hydroxy-3,4-dihydrocarbostyril (0.18 mol), 49.09 g of 1-cyclohexyl-5-(4-chlorobutyl)-1,2,3,4-tetrazole (0.20 mol), 101.63 g of potassium carbonate (0.74 mol), 1.5 g of sodium sulfite (0.01 mol), 20.43 g of 50% aqueous solution of tetrabutylammonium chloride (0.04 mol), and 150 ml of water. The mixture of the reactants was heated at about 85° C. (80 to 90° C.) for 6 hours with circulating by continuous disperser (pipeline homomixer T.K.ROBO MIX manufactured by TOKUSHUKIKA KOGYO CO. LTD.). After the completion of the reaction, the reaction mixture was cooled to around 20° C., and the precipitated crystalline product was collected by filtration and washed with 150 ml of water (5 times volume). The obtained crystalline product was introduced into a flask having a capacity of 1 L, and washed with 600 ml of water under stirring at about 90° C. for about 1 hour. The solution thus obtained was cooled, and the crystal was collected by filtration and washed with 150 ml of water (5 times volume), then dried at about 80° C. for 10 hours. Thus, 67.40 g (yield: 99.23%) of 6-[4-(1-cyclohexyl-1,2,3,4-tertazol-5-yl)butoxy]-3,4-dihydrocarbostyril was obtained.

Then, 60 g of the crystal obtained and 90 ml of methanol were introduced into a flask having a capacity of 1 L, and the crystal was washed with stirring at about 25° C. for about 10 minutes. After cooling the mixture, the crystal was collected by filtration and washed with 45 ml of methanol. The crystal obtained was dried at about 80° C. for 10 hours to obtain 58.18 g (yield: 96.97%) of 6-[4-(1-cyclohexyl-1,2,3,4-tertazol-5-yl)butoxy]-3,4-dihydrocarbostyril as colorless needle-like crystal.

Purity: 99.73%; m.p.: 158–159° C.

The total yield of the objective 6-[4-(1-cyclohexyl-1,2,3,4-tertazol-5-yl)butoxy]-3,4-dihydrocarbostyril was 96.22%. The purity was measured by high performance liquid chromatography (HPLC) under the same conditions as in Example 1.

What is claimed is:

1. A process for producing a carbostyril derivative represented by the following general formula (I):

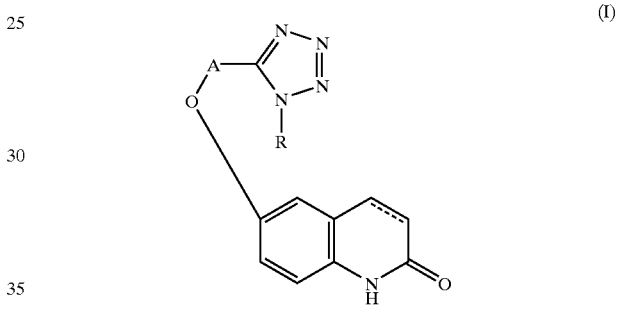

wherein A represents a group of the formula: —(CH$_2$)$_4$—, R represents a cyclohexyl group, and the bond between the 3- and 4-positions of the carbostyril skeleton represents a single bond, the process comprising:

reacting a carbostyril derivative represented by the following general formula (II):

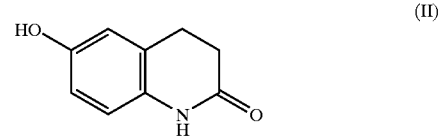

with a tetrazole derivative represented by the following general formula (III):

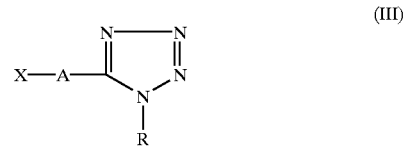

wherein X represents a halogen atom, and A and R are as defined above, and wherein the reacting occurs in an aqueous single phase.

2. A process for producing a carbostyril derivative according to claim 1, wherein X in the tetrazole derivative represented by general formula (III) is a chlorine atom.

3. A process for producing a carbostyril derivative according to claim 1, wherein the reaction is carried out in the presence of an agent of preventing coloration caused by oxidation.

4. A process for producing a carbostyril derivative according to claim 3, wherein the agent of preventing the coloration caused by oxidation is sodium sulfite.

5. A process for producing a carbostyril derivative according to claim 1, wherein the reaction is carried out by circulating a solution of the reaction mixture with continuous disperser.

6. A process for producing a carbostyril derivative according to claim 1, wherein said aqueous single phase further comprises a catalyst.

7. A process for producing a carbostyril derivative according to claim 6, wherein said catalyst is a quaternary ammonium salt catalyst.

8. A process for producing a carbostyril derivative according to claim 7, wherein said quaternary ammonium salt catalyst is substituted with at least one residue chosen from straight and branched chain alkyl groups having 1–18 carbon atoms, phenyl lower alkyl groups, and phenyl groups, and wherein the salt forming ion of said quaternary ammonium salt is a halogen ion.

9. A process for producing a carbostyril derivative according to claim 8, wherein said quaternary ammonium salt catalyst is substituted with at least one group chosen from straight and branched chain alkyl groups having 1–18 carbon atoms.

10. A process for producing a carbostyril derivative according to claim 9, wherein said quaternary ammonium salt catalyst is tetrabutylammonium chloride.

11. A process for producing a carbostyril derivative according to claim 7, wherein the salt-forming ion of said quaternary ammonium salt catalyst is chosen from a hydroxyl ion, a hydrogen sulfate ion, and a halogen ion.

12. A process for producing a carbostyril derivative according to claim 7, wherein said quaternary ammonium salt catalytst is used in an amount ranging form 0.1 to 0.5 mol per mol of the compound of general formula (II).

13. A process for producing a carbostyril derivative according to claim 1, wherein said aqueous single phase further comprises a base.

14. A process for producing a carbostyril derivative according to claim 13, wherein said base is an inorganic base.

15. A process for producing a carbostyril derivative according to claim 14, wherein said inorganic base is chosen from potassium carbonate, cesium carbonate, lithium carbonate, lithium hydroxide, lithium hydrogen carbonate, sodium hydroxide potassium hydroxide, potassium hydrogen carbonate, sodium carbonate, sodium hydrogen carbonate and mixtures thereof.

16. A process for producing a carbostyril derivative according to claim 1, wherein said aqueous single phase comprises at least one solvent.

17. A process for producing a carbostyril derivative according to claim 16, wherein said at least one solvent consists essentially of water.

18. A process for producing a carbostyril derivative according to claim 17, wherein said at least one solvent is water.

19. A process for producing a carbostyril derivative according to claim 1, wherein the compound (III) is used in an amount ranging from 1.1 to 1.5 mol per mol of the compound (II).

20. A process for producing a carbostyril derivative according to claim 1, wherein the reaction temperature ranges from 50° C. to 150° C.

* * * * *

UNITED STATES PATENT AND TRADEMARK OFFICE
CERTIFICATE OF CORRECTION

PATENT NO. : 6,630,590 B1
DATED : October 7, 2003
INVENTOR(S) : Shinji Aki et al.

It is certified that error appears in the above-identified patent and that said Letters Patent is hereby corrected as shown below:

Title page,
Item [63], Related U.S. Application Data, should read:
-- Continuation-in-part application of application No. 09/869,264, filed August 5, 2002, which is a 371 application of application No. PCT/JP01/03803, filed May 2, 2001, now abandoned. --

Column 10,
Line 3, "form" should read -- from --.
Line 15, "hydroxide potassium" should read -- hydroxide, potassium --.

Signed and Sealed this

Twenty-first Day of December, 2004

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,630,590 B1 |
| APPLICATION NO. | : 10/208740 |
| DATED | : October 7, 2003 |
| INVENTOR(S) | : Shinji Aki et al. |

It is certified that error appears in the above-identified patent and that said Letters Patent is hereby corrected as shown below:

In the specification under "Cross-Reference to Related Application:"
Col. 1, lines 8-10, should be replaced with:
-- This application is a continuation-in-part application of U.S. Serial No. 09/869,264 (now abandoned), which is the national stage application of International Application No. PCT/JP01/03803, filed May 2, 2001, the contents of which are all incorporated herein by reference.--

Signed and Sealed this

Sixth Day of March, 2007

JON W. DUDAS
*Director of the United States Patent and Trademark Office*